(12) United States Patent
Smith et al.

(10) Patent No.: US 8,900,141 B2
(45) Date of Patent: Dec. 2, 2014

(54) INTEGRATED METHOD AND SYSTEM FOR DIAGNOSIS DETERMINATION

(75) Inventors: William Kennedy Smith, Chicago, IL (US); John Creed, Chicago, IL (US); James Christensen, Escondido, CA (US)

(73) Assignee: Medred, LLC, Chicago, IL (US)

( * ) Notice: Subject to any disclaimer, the term of this patent is extended or adjusted under 35 U.S.C. 154(b) by 1365 days.

(21) Appl. No.: 11/707,274

(22) Filed: Feb. 16, 2007

(65) Prior Publication Data

US 2007/0197882 A1 Aug. 23, 2007

Related U.S. Application Data

(60) Provisional application No. 60/774,197, filed on Feb. 17, 2006, provisional application No. 60/872,478, filed on Dec. 4, 2006.

(51) Int. Cl.
*A61B 5/00* (2006.01)
*G06F 19/00* (2011.01)

(52) U.S. Cl.
CPC .......... *G06F 19/3443* (2013.01); *G06F 19/324* (2013.01); *A61B 5/0002* (2013.01)
USPC ............................... 600/301; 600/300; 705/3

(58) Field of Classification Search
USPC ....................................... 600/300, 301; 705/2
See application file for complete search history.

(56) References Cited

U.S. PATENT DOCUMENTS

| | | | |
|---|---|---|---|
| 5,769,074 A * | 6/1998 | Barnhill et al. | 600/300 |
| 6,641,532 B2 * | 11/2003 | Iliff | 600/300 |
| 7,149,756 B1 * | 12/2006 | Schmitt et al. | 600/300 |
| 7,297,113 B1 * | 11/2007 | Russell et al. | 600/302 |
| 2002/0133377 A1 * | 9/2002 | Brown | 705/3 |
| 2003/0013944 A1 * | 1/2003 | Benja-Athon | 600/300 |
| 2003/0050803 A1 * | 3/2003 | Marchosky | 705/3 |
| 2004/0117215 A1 * | 6/2004 | Marchosky | 705/3 |
| 2005/0010444 A1 * | 1/2005 | Iliff | 705/2 |
| 2005/0033121 A1 * | 2/2005 | Modrovich | 600/300 |
| 2006/0135859 A1 * | 6/2006 | Iliff | 600/300 |
| 2006/0161459 A9 * | 7/2006 | Rosenfeld et al. | 705/3 |
| 2007/0088559 A1 * | 4/2007 | Kim | 705/1 |
| 2008/0091086 A1 * | 4/2008 | Legere et al. | 600/300 |
| 2014/0081666 A1 * | 3/2014 | Teller et al. | 705/3 |

* cited by examiner

*Primary Examiner* — William Thomson
*Assistant Examiner* — Bobby Soriano
(74) *Attorney, Agent, or Firm* — Arent Fox LLP

(57) ABSTRACT

A method and system for creating a database for diagnosis determination that includes receiving baseline symptoms in a memory, receiving diagnoses in the memory, classifying the diagnoses that correspond to the baseline symptoms as diagnoses linked to the baseline symptoms, and rendering the diagnoses accessible on the basis of the corresponding baseline symptoms. A method and system for determining a diagnosis and treatment that includes receiving patient symptoms, comparing patient symptoms to previously stored baseline symptoms, identifying the patient symptoms that correspond to the baseline symptoms, and providing diagnoses that correspond to the identified patient symptoms to a user.

38 Claims, 14 Drawing Sheets

FIG. 9

INTEGRATED METHOD AND SYSTEM FOR DIAGNOSIS DETERMINATION

This application claims priority from U.S. provisional application No. 60/774,197, filed Feb. 17, 2006, and U.S. provisional application No. 60/872,478, filed Dec. 4, 2006, each of which is incorporated herein by reference in its entirety.

BACKGROUND OF THE INVENTION

1. Field of the Invention

The present invention relates to a method and system for diagnosis of a patient based on the patient's symptoms. Specifically, the present invention relates to a method and system for the automated determination of the appropriate diagnosis of a patient on the basis of the patient's symptoms.

2. Background of the Related Art

As it may be difficult for elderly people, people with disabilities or poor people to have access to a doctor in an adequate or optimal amount of time, a medical system for automatic diagnosis of patients is becoming increasingly desirable. For example, Akasaka et al. (U.S. Pat. No. 5,785,650), which is incorporated herein by reference in its entirety, teaches an integrated medical system that allows the transmission of patient data via a network to a remote medical practitioner.

A patient can utilize such a prior art system while being at home. Such a prior art system allows data, such as blood pressure and electrocardiogram output, to be automatically transmitted. Such a system also allows the patient to input personal data, such as body weight, via a keyboard at a communication terminal or to provide his/her answers to questions posed to the patient by the system.

On the other hand, Walker et al. (U.S. Pat. No. 6,302,844), which is incorporated herein by reference in its entirety, teaches a method and apparatus for analyzing data from remote monitoring equipment and determining whether an anomalous event has occurred, and whether the anomalous event warrants contacting a physician. Morris et al. (U.S. Patent Application No. 2004/0078227), which is incorporated herein by reference in its entirety, teaches a system and method that are used for creating a longitudinal medical record for an injured person and includes a plurality of mobile computing devices having an interface for receiving information from a first responder or a health care practitioner.

However, none of the se systems provide an automated diagnosis method and system that provides a patient with a viable diagnosis and treatment on the basis of symptoms and other information provided by the patient.

SUMMARY OF THE INVENTION

In light of the above described problems and shortcomings, as well as others, various exemplary embodiments according to this invention provide methods and systems for creating a database for diagnosis determination, the method including receiving one or more baseline symptoms in a memory, receiving one or more diagnoses in the memory, classifying the diagnoses that correspond to the baseline symptoms as diagnoses linked to the baseline symptoms, and rendering the diagnoses accessible on the basis of the corresponding baseline symptoms.

Other exemplary embodiments according to this invention provide methods and systems for determining a diagnosis and treatment, the method including receiving patient symptoms, comparing patient symptoms to previously stored baseline symptoms, identifying the patient symptoms that correspond to the baseline symptoms, and providing one or more diagnoses that correspond to the identified patient symptoms.

Details of these and other advantages and novel features of the invention may be set forth in part in the description that follows, and in part may become more apparent to those skilled in the art upon examination of the following or upon learning by practice of the invention.

BRIEF DESCRIPTION OF THE DRAWINGS

Various exemplary embodiments of the systems and methods may be described in detail, with reference to the following figures, wherein:

FIG. 9 is an illustration of an exemplary display screen for vitals;

DETAILED DESCRIPTION OF THE INVENTION

These and other features and advantages of this invention are described in, or are apparent from, the following detailed description of various exemplary embodiments of the systems and methods according to this invention.

Figure 1:
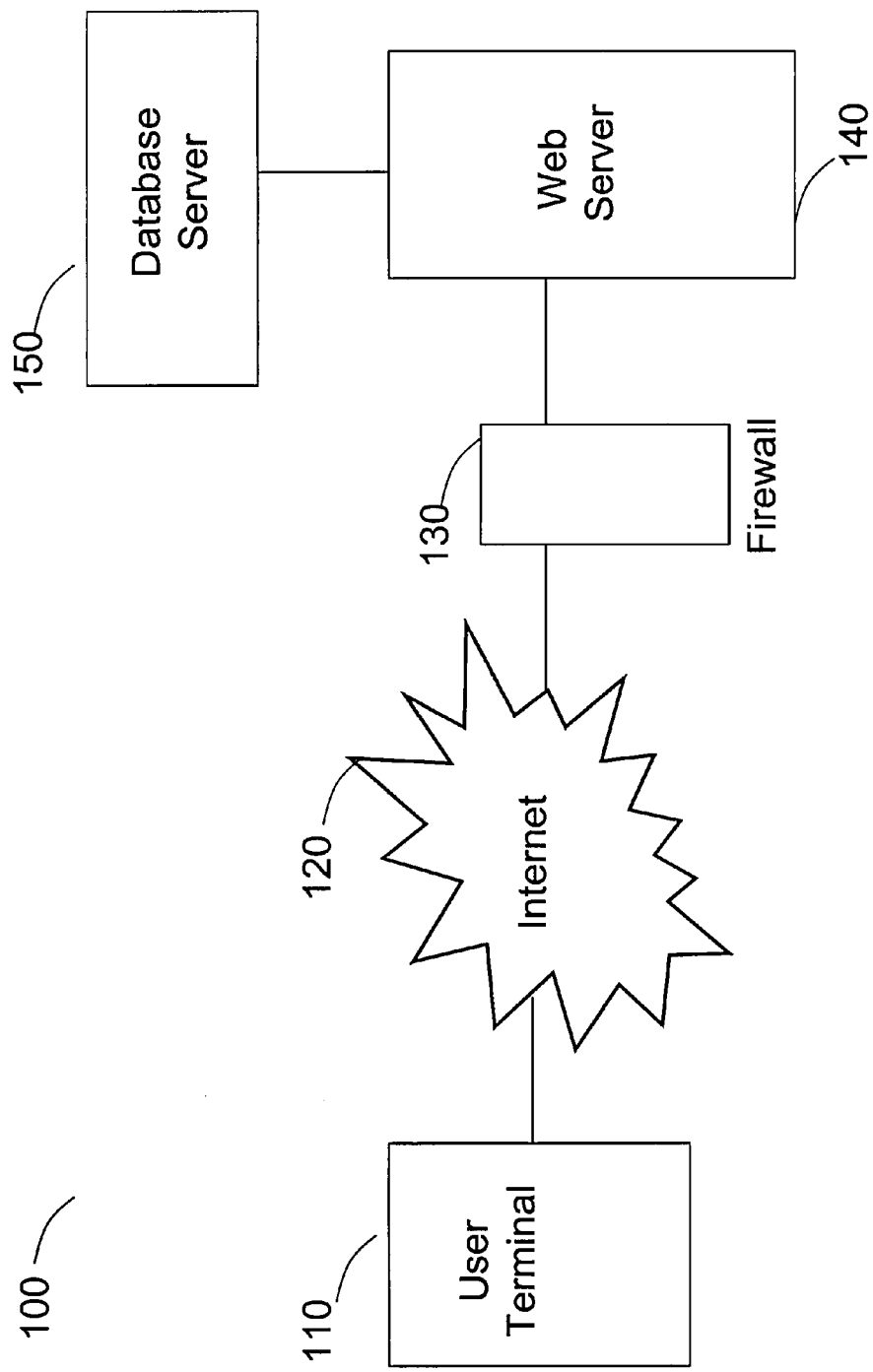
FIG. 1 is an illustration of a system for diagnosis determination according to an exemplary embodiment of the present invention.

FIG. 1 is an illustration of a system for diagnosis determination according to an exemplary embodiment of the present invention. In FIG. 1, the system 100 includes a user terminal 110, operated by a user and connected to a server 140 such as a web server. Users may have varying levels of access to system functions and ability to interact, such as, for example, add and change data in the system or perform operations, depending on the user's access level. For example, a user access level may be added to security information upon access of the system, such as user name and password. According to various exemplary embodiments, the server 140 may be a remote server, and the user terminal 110 is connected to the server 140 via a network 120, such as the Internet. Also, the server 140 may be protected by a firewall 130, and may be connected to a data repository 150, such as a database server. In operation, a user may enter information into the user terminal 110. The information may be, for example, symptoms of an ailment or of an abnormal physical or mental condition. The information entered by the user may then be transmitted via the network 120 to the server 140. Once the information is received by the server 140, the information is used to determine a diagnosis, and possibly a treatment by matching information for similar symptoms stored in the data repository 150. According to various exemplary embodiments, the data repository 150 may contain a number of symptoms, and combinations of symptoms, and any corresponding diaganoses and treatments. The diagnoses and treatments of that correspond to the number of symptoms are determined on the basis of current medical knowledge and experience.

The data repository 150 database is a collection of records or information which is stored in a computer in a systematic or structured way, so that a user, via a computer program, for example, may consult it to answer queries. The computer program used to manage and query a database may be or include a database management system. The records retrieved in response to queries become information that can be used to make diagnosis and treatment decisions. The database may be queried via a series of computer screens prompting the user, whether a patient or health care practitioner, to enter the symptoms suffered by the patient. According to various exemplary embodiments, the various computer screens vary from providing very broad queries to more specific ones on the basis of the responses entered for the broad queries.

Figure 2:
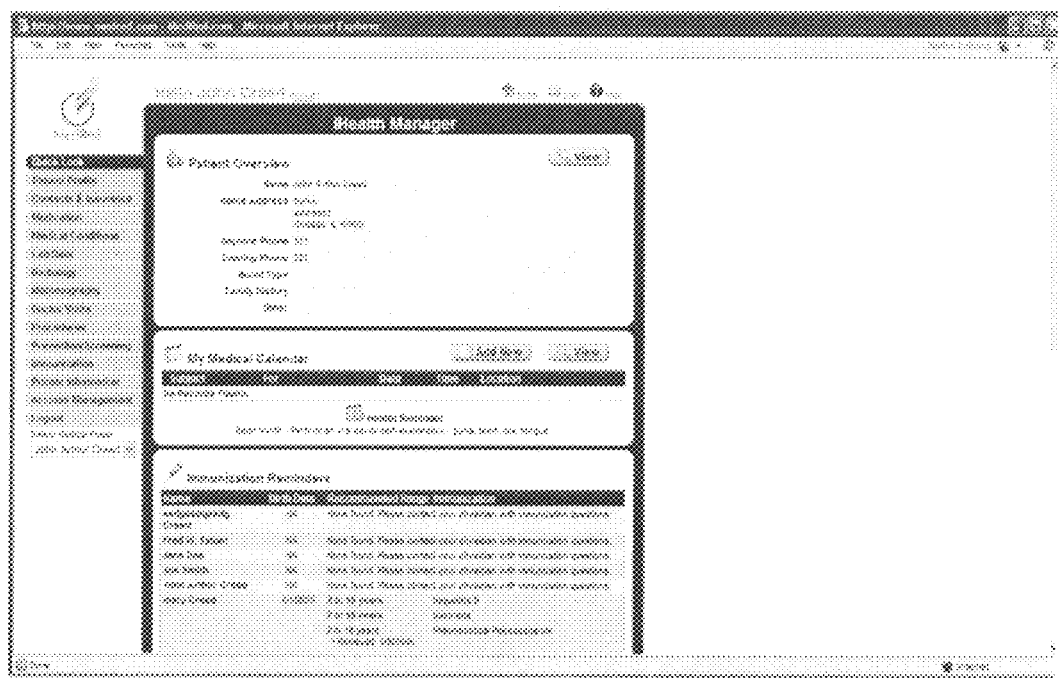
FIG. 2 is an illustration of an exemplary user interface screen.

FIG. 2 is an illustration of an exemplary user interface screen. In FIG. 2, the screen may include of the following sections: Quick Look, Patient Profile, Contacts & Insurance, Medication, Medical Conditions, Laboratory Data, Radiology, Mammography, Doctor Visits, Procedures, Prevention/Screening, Immunization, Private Information, Document Inbox, or Account Management. Each of these sections can be accessed and/or modified by subscribers at will. The data that is entered in each of these sections may be stored in a centralized data repository. According to various exemplary embodiments, each section may include detail listing views, Add New functionality and Edit functionality. Screens may be navigated using buttons incorporated per section. It should be noted that the informational display views may be segregated by topic to allow for quick browsing and easy to understand viewing.

For example, once a user accesses the product via successful login, the user may have the ability to navigate through electronic medical records using the navigation options listed to the left of the content window in FIG. 2. Data additions or edits may be performed using a combination of data entry text boxes and a series of point-and-click drop-down boxes pre-populated with data. Users may have the ability to enter personal, emergency and physician contact information, along with basic identifying information, such as name, address, telephone number, and the like, using the data entry text boxes. Medical related information that requires users to enter procedure or test names, medication titles or medical conditions may be selected from the prepopulated drop down lists. The system website may be developed to provide users with standard access via a network, such as the Internet. This standard access encompasses standard security features, such as use of a username and password combination. When a valid username and password combination are submitted to the application and validated, the user may have access to the medical record system at a level associated with that user.

For example, the Quick Look section may provide a user with a high level overview of pertinent data, such as the listing screens for the patient information, a medical calendar, a list of allergies and/or drug reactions, an immunization reminder area, a medication listing, a current medical condition list and medical history. Print capabilities may be available at the top of the screen to allow users to gain access to a hard copy of this section. The Patient Profile section may provide the user with a view of patient contact information and medical information that is constant and unlikely to change, such as known allergies and medical background information. The background information may track data that can relate to health habits, such as occupation, alcohol and drug intake, caffeine intake, and the like. Users can also provide a relevant overview of basic health information such as blood type, date of birth, Human Immunodeficiency Virus (HIV) status and domestic violence exposure. The Contacts & Insurance section may allow the user the ability to enter emergency, physician and insurance contact and coverage information, including addresses, telephone numbers and email addresses. The Insurance portion of this section may provide the user with a central location for storing all active insurance information. This area may allow users to enter/update primary insurance provider. The Medication section may provide the user with a comprehensive listing of medications, including, for example, name, start date or end date and dosage information. The default view of this section may include a 12-month drug usage graph that provides the user with a graphical view of the patient's medication intake.

The Medical Conditions section may provide the user with an area to enter, update and track medical conditions. The default view of this section may provide a complete list of all entered conditions, and users have the option to enter more detail, post notes to each condition or add new conditions as needed. The Laboratory Data section may include a tracking program for laboratory and related medical testing information. It may include blood pressure, pulse, blood type, complete blood count (CBC), and cholesterol, for example laboratory results can be uploaded to a health manager to manage medical record for future reviews by physicians. The Radiology section may allow users to track radiology, medical, and surgical data. A user can enter the procedure type, additional notes and upload images to a patient's medical folder. The Mammography Information section may include a Mammography History, including the year of the mammogram, results, classification and location of the actual report. Users can upload actual mammogram reports to this section if desired. The Doctor Visits section may allow users to record doctor visits, including date of visit, reason for visit and the outcome for each visit. The Procedures section may allow procedures to be coordinated and consolidated chronologically. This section may provide users with additional backup information to assist in having a more complete personal medical record. This section may track such procedures as electrocardiograms, pap smears, glaucoma, podiatry, and certain dental information. The Prevention/Screening section may allow users to log all of the preventative measures and/or screening tests that have been completed. Users can enter the dates of the tests, as well as the test outcome.

The Immunization section may allow users to enter and track immunization information. The default view of this section may list all entered immunizations; the user has the ability to add/update records. The Private Information section may provide the user with an area to enter additional information that may be categorized as private. This information can include daily journal type entries related to diet and exercise. This section may be used to track daily insulin intake and/or sugar levels for diabetics, for example. The Document Inbox section may provide the user with an area to manage faxed documents within a patient's account. Users have the ability to select individual electronic documents and associate them to specific areas within the patient's medical record. The Account Management section may provide the user with a section to manage account information, including features for setting up multiple family members per account. This section may allow users to set up additional individuals who may need to gain access to the medical record account; this can include any individual the user grants access to, including personal physicians, emergency contacts, and the like. Security measures can be selected per individual, as users can select which sections the individual can have access to and whether or not edit capabilities are allowed for the individual.

Figure 3A:
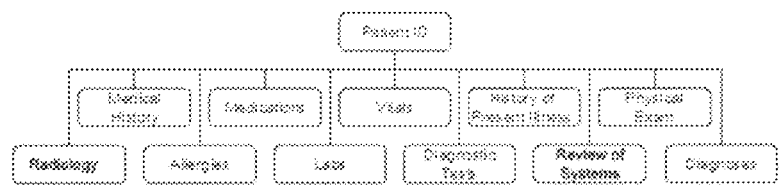
FIGS. 3(a)-(b) are illustrations of functional requirements according to an exemplary embodiment of the present invention.
Figure 3B:
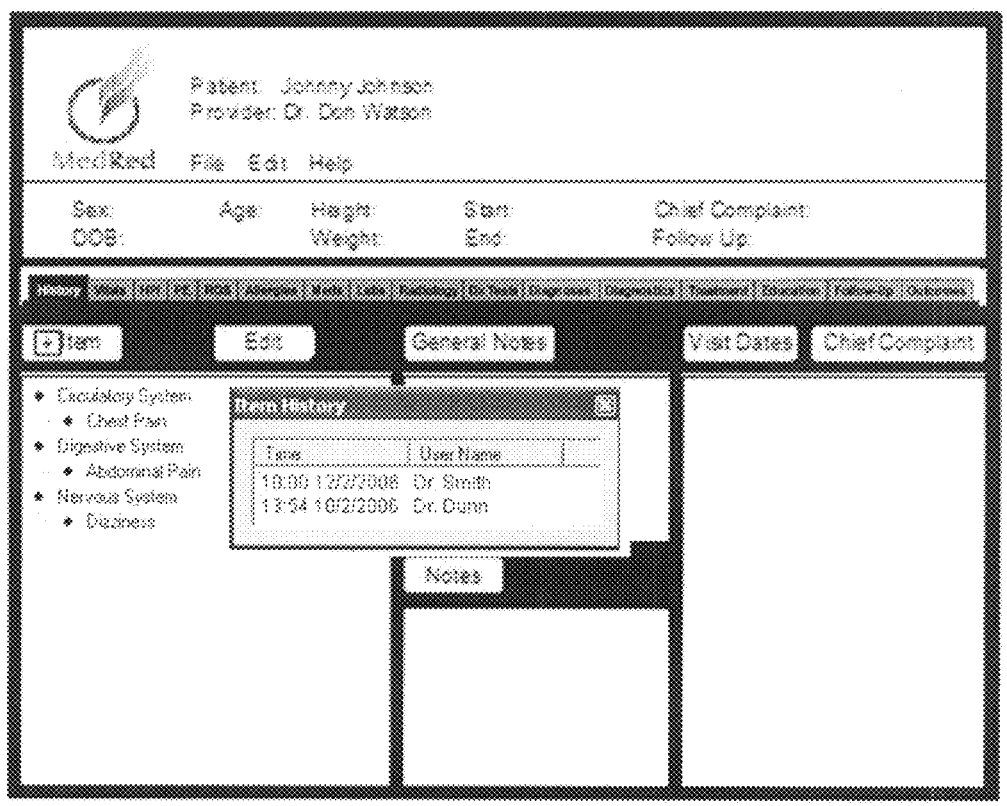

FIGS. 3(a)-(b) are illustrations of functional requirement screens according to an exemplary embodiment of the present invention. The patient medical record may be entered through a series of point and click graphical user interfaces (GUI). The GUI for each primary element is described further below. A Select Patient chart may first be displayed. The names of existing patients and any identification numbers assigned to each patient may be displayed. A user may scroll through the list or search for a patient by last name or identification number. A patient may also be added on the screen that may display information via, for example, a pop-up window with the fields and allow the user to enter data, such as name, identification number (ID), sex, and date of birth. Existing patient data may be similarly edited. Multiple patient charts may be open at any time. For example, a health provider may enter the reason for a patient's visit to open the patient chart. The provider may select from a displayed list, enter the reason for the visit, or simply follow-up on the patient's visit by entering free text. A focused assessment feature may also help guide the user, such as the provider, through the set of signs and symptoms that should be evaluated for a given reason for the patient's visit. This guidance may be provided by highlighting appropriate items in the assessment pages. For example, items related to a reason for the patient's visit for a cough may be highlighted in History, Physical Exam, and Medications sections of the interface.

According to various exemplary embodiments, Primary Element buttons may display secondary elements, such as History, Vitals, History of Present Illness, and the like, in another window. Data charted within the selected element during the current visit may also be displayed. Current data and previously charted data may also be displayed for History, Allergies, Diagnoses, Diagnostics, Treatment, Education, Follow-Up, and Outcomes. Other information, such as history of patient visits, including the date and time of each visit and the associated Reason for the patient's visit or Follow Up, may further be displayed. Furthermore, historical state information may be displayed, along with the username of the user who entered the state information, along with the dates this information was charted, as shown in the Item History. Thus, the health provider is able to chart medical history by selecting one of a plurality of check boxes, as discussed above. Notes may also be added to any chart.

A search option may also be available to allow a user to navigate the chart hierarchy. Results of the search may be displayed in a search results window, which includes the hierarchy path to the search entry. Furthermore, recorded allergies, such as the patient's reaction and the date the allergy was recorded, may also be displayed at the user's request. New allergies and the patient's reaction are recorded from a predefined selection list, or the user, such as a health provider, may enter a new allergy and reaction as free text. New medications may be recorded from a predefined selection list, or the provider may enter a new medication as free text. Laboratory results may also be entered by selecting from a predefined selection list. Selection from the predefined category list may display a predefined list of laboratory orders. Selection of a laboratory order displays a predefined test name. Selection of a test name may display the normal limits for the given test and may allow the user to enter the laboratory result. Finally, the user may enter diagnostic test results by selecting from a predefined check list. Selection from the list may display a predefined check list of defined tests. Selection of a result may add the diagnostic test and result to the patient chart.

Figure 4:
FIG. 4 is an illustration of an exemplary assisted diagnosis display in accordance with embodiments of the present invention.

FIG. 4 is an illustration of an exemplary assisted diagnosis display screen. In FIG. 4, an exemplary list of potential diagnoses generated by the method or system of the present invention as recommendations to the health provider are displayed, as well as a list of the clinical decisions made by the provider. The differential diagnosis list may be based on patient data processed through decision support modules. Each recommendation may include a likelihood generated by the system, which provides a level of confidence associated with the recommendation. There are four possible likelihoods displayed in decreasing order of confidence in the exemplary application shown in FIG. 4. The different likelihoods include: 1) "Consider," which means that the signs and symptoms are consistent with the diagnosis; 2) "Rule Out," which means that the signs and symptoms are consistent with the diagnosis and sufficiently relevant that the system recommends further investigation or diagnostic testing associated with the diagnosis; 3) "Probable," which means that the signs and symptoms and/or diagnostic results are highly relevant to the diagnosis; and 4) "Confirm," which means that the signs and symptoms and/or diagnostic results are highly relevant to the diagnosis, and laboratory results are sufficient to provide high confidence. System Recommendations may or may not be recorded in the patient medical record. A diagnosis may only be recorded when the provider makes a Clinical Diagnosis by setting the final status of a recommendation.

The provider or other authorized user may move any of the System Recommendations to the top of the screen, where they become Clinical Decisions by first selecting the recommendation from the list and then selecting the 'Status' button, for example. The provider may then set the Status as 'Confirmed,' 'Probable,' 'Potential,' or 'Ruled Out.' The system may insert the date of the decision (e.g., automatically), which may be edited by the provider to record a previously determined clinical decision. When editing the date of the decision or entering any other data in the patient record, the system may record (e.g., automatically) the time and date of the entry in the database. The provider may also change the status of an existing Clinical Decision by first selecting the decision and then selecting 'Status.' Clinical Decisions may be displayed chronologically, with the most recent decision at the top of the list.

The provider or other authorized user may also set a clinical decision for a diagnosis that does not appear in the system generated differential diagnosis list by adding a diagnosis from the full list of diagnoses included in the system. These diagnoses may appear, for example, in a drop down menu. The provider may then select the appropriate diagnosis and set the Status as described above. If the diagnosis is not included in the drop down menu, the provider may also type the diagnosis in a blank field provided in the menu. An icon or button may also be provided to display a pop-up check list that includes all elements of an embedded protocol for that specific diagnosis. The icon may be linked to elements that have been charted for the specific patient, thus providing a rationale for the recommendation. The provider may remove any checked element from the patient chart by selecting a checked box, or chart additional patient data by selecting elements that are not checked. Either action, once saved, may cause patient data to be reprocessed through all protocols that contain the checked or unchecked elements.

According to various exemplary embodiments of the present invention, a history of all Clinical Diagnoses that have been entered for the current patient may also be displayed, but only the most recent status and date of each diagnosis. The full history of a particular diagnosis may be presented in a pop-up display by selecting the diagnosis. Furthermore, the health provider may attach notes to a Clinical Decision, and a pop-up edit screen may be displayed that includes any notes previously attached to the decision and allows the provider to add new or additional notes.

Figure 5:
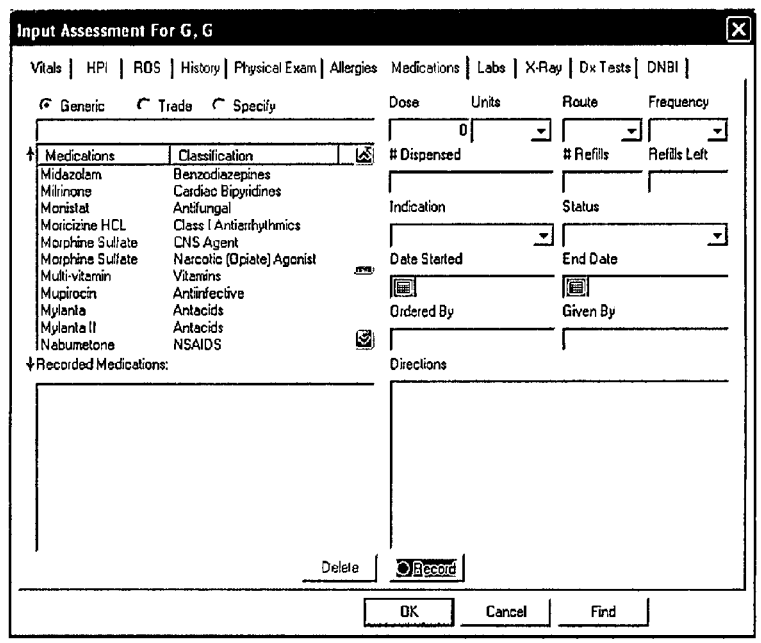
FIG. 5 is an illustration of an exemplary recommended treatment produced in accordance with exemplary implementations of a method and system of the present invention.

FIG. 5 is an illustration of an exemplary recommended treatment screen in accordance with an embodiment of the present invention. According to various exemplary embodiments, the listing of the diagnostics found may be based upon the likelihood of the diagnosis, such as, as discussed above, Consider, Rule Out, Probable, or Confirm. For example, if a recommended treatment is selected by a user by, for example, clicking on an icon, the full path to the recommended treatment may be highlighted to allow the user to focus on that treatment. An example is shown in FIG. 5, where Morphine Sulfate has been highlighted as the result of a treatment recommendation. As a navigational aide to the user, note that small arrows may also appear at the top and bottom of the Medications list. These arrows indicate that additional items have been highlighted by the refocused assessment process. Selecting either of these arrows causes the Medications window to scroll to the next highlighted medication. The listing of the diagnostics found will be based upon the likelihood of the diagnosis: Consider, Rule Out, Probable, or Confirm.

Furthermore, data mining reports may be generated to provide summary reports, such as Medical Encounter Summary, Diagnoses Report, Symptom Report, and Intervention Report. According to various exemplary embodiments, the Medical Encounter Summary report allows the user to select a start date and an end date of the report. The report may also display summary statistical data, as shown at the bottom of the figure. The Diagnosis Report allows the user to select a particular problem and (e.g., status from drop down menus), and to display summary statistical data. The Symptom Report allows the user to select several levels of symptoms from, for example, drop down menus, and may display summary statistical data. The Intervention Report allows the user to select the type of intervention (Diagnostics, Treatment, Education, or Follow-Up), or a particular intervention and the status of interventions (All, Done, Ordered, or Pending).

Figure 6:
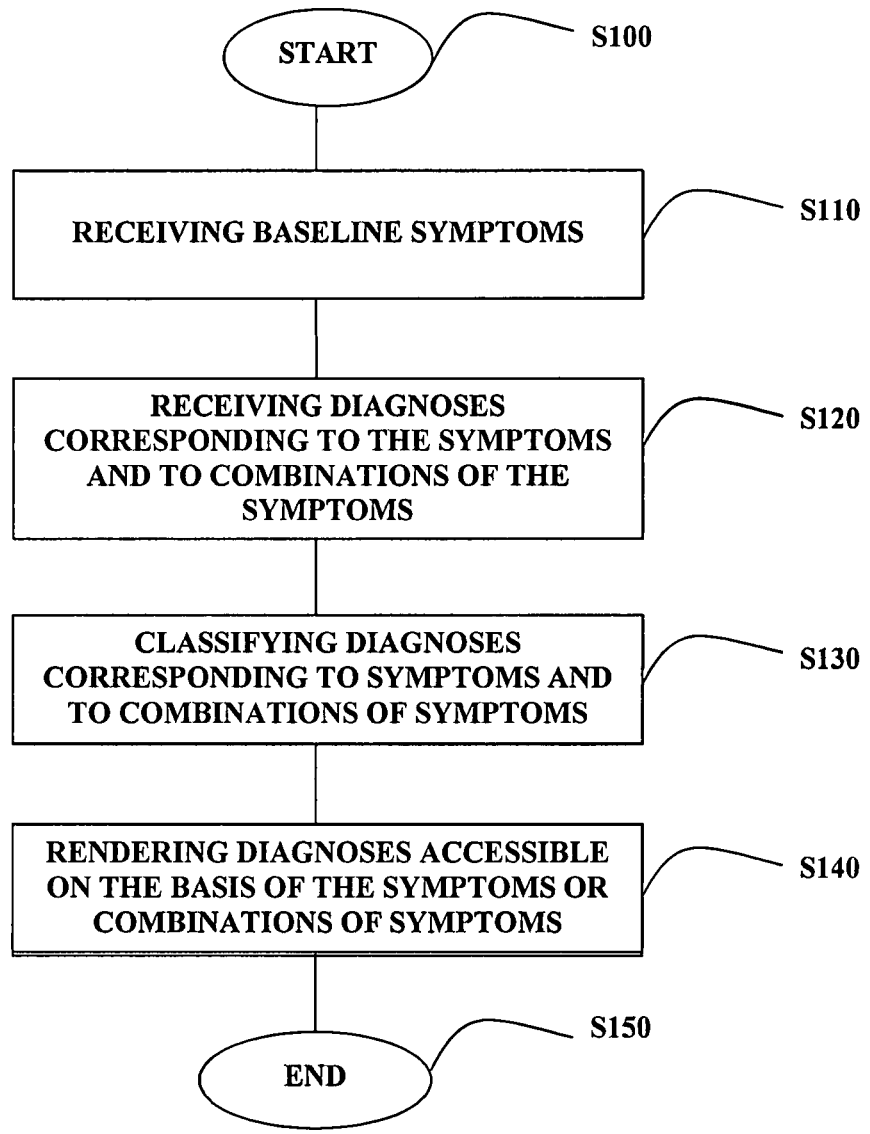
FIG. 6 is a flow chart illustrating a method for creating a database for diagnosis determination according to an exemplary embodiment of the present invention.

FIG. 6 is a flow chart illustrating a method for creating a database for diagnosis determination, in accordance with an exemplary embodiment of the present invention. In FIG. 6, the method starts in step S100 and continues to step S110, where baseline symptoms are received. For example, baselines symptoms may be any symptoms currently known to have occurred on people or animals, and that are symptomatic of an abnormal physical or mental condition. Baseline symptoms may be a headache, chest pain, bleeding, loss of consciousness, temporary loss of vision, and the like. When received, the baseline symptoms may be stored in memory. Next, the method continues to step S120, where the various diagnoses corresponding to the received symptoms are also received and stored in memory. For example, a diagnosis of "stroke" may be entered as corresponding to the baseline symptom "loss of consciousness." Also, a plurality of diagnoses may be received that correspond to the same baseline symptom. For example, not only a diagnosis of "stroke" may be received as corresponding to the baseline symptom "loss of consciousness," but also a diagnosis of "heat exhaustion" or "emotional trauma" can be received that corresponds to the same baseline symptom of "loss of consciousness." Furthermore, other diagnoses may be received that correspond to not only one baseline symptom, but to a combination of baseline symptoms. For example, the diagnosis "stroke" may be received as corresponding to the combination of "loss of consciousness" and "loss of the ability to speak." Accordingly, the combination of the two baseline symptoms "loss of consciousness" and "loss of the ability to speak" effectively results (i.e., through a decision tree function in the software) in the elimination of the diagnoses "heat exhaustion" and "emotional trauma" because the combination of the two baseline symptoms is more likely to correspond to the diagnosis "stroke" than to any one of the other two possible diagnoses. Thus, another class of diagnoses can be received that corresponds to a combination of baseline symptoms, such that a smaller number of possible diagnoses is received because these diagnoses correspond to a combination of baseline symptoms.

Ultimately, if a large enough number of baseline symptoms are combined, only one corresponding diagnosis may be associated with this combination and stored in memory. Furthermore, the diagnoses may be regularly updated on the basis of the latest medical progress. Next, the method continues to step S130, where the various received diagnoses are classified in terms of the baseline symptoms to which they correspond, and in terms of any combinations of baseline symptoms to which they correspond. For example, the diagnosis "stroke" can be classified as being a possible diagnosis for each baseline symptom "loss of consciousness," "garbled language," and "loss of vision," and also for being a possible diagnosis for any combinations of these three baseline symptoms. Next, the method continues to step S140, where the diagnoses are rendered accessible on the basis of the baseline symptoms. In other words, an interface may be made available to a user to allow the user to associate the different diagnoses and their corresponding symptoms or combinations of symptoms for access for diagnosis and treatment purposes based on symptoms and other information. Next, the method continues to step S150, where the method ends.

It should be noted that various symptoms may be assigned different weight in the determination of a final diagnosis. For example, the symptom of "loss of the ability to speak" may be assigned a greater weight than the symptom of "loss of consciousness" in the determination of the diagnosis of a "stroke." Furthermore, other symptoms may be assigned a different weight because, for example, they may eliminate a given diagnosis. For example, the symptom "belly ache" may be weighted negatively in relation to the diagnosis "stroke." In other words, if the symptom "belly ache" is received, then the diagnosis "stroke" may be eliminated from the list of possible diagnoses.

Figure 7:
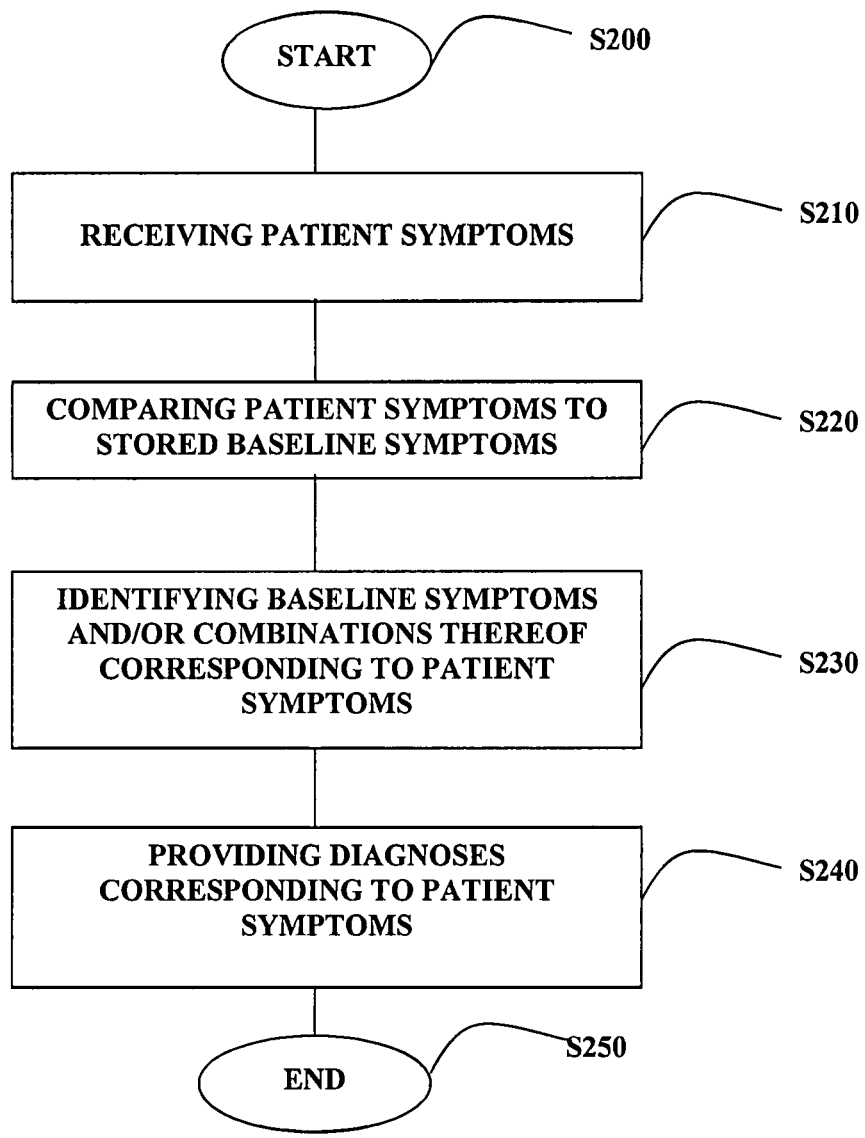
FIG. 7 is a flow chart illustrating a method for determining a diagnosis and treatment according to an exemplary embodiment of the present invention.

FIG. 7 is a flow chart illustrating a method for determining a diagnosis and treatment according to an exemplary embodiment of the present invention. In FIG. 7, the method starts in step S200 and continues to step S210, where patient symptoms are received. For example, patient symptoms may be any symptoms currently known to have occurred on a patient, and that are symptomatic of an abnormal physical or mental condition of the patient. Patient symptoms may be a headache, chest pain, bleeding, loss of consciousness, temporary loss of vision, and the like. Next, the method continues to step S220, where the received patient symptoms are compared to the stored baseline symptoms. According to an exemplary embodiment, the patient symptoms are compared to every single baseline symptom stored in memory, and in the case of a combination of patient symptoms, that combination is compared to every combination of baseline symptoms stored in memory. Next, control continues to step S230, where all the baseline symptoms that correspond to the patient symptoms are identified. According to an exemplary embodiment, in the case where a combination of patient symptoms is received, then either all or a part of the patient symptoms of that combination are identified to one or more combinations of baseline symptoms on the basis of a similarity between patient symptoms and baseline symptoms. Next, the method continues to step S240, where the diagnoses that correspond to any identified baseline symptom, or to any identified combination of baseline symptoms, as corresponding to the patient symptoms, are provided to a user. For example, the diagnoses may be displayed on a computer screen, or printed out on an imaging medium. Next, the method continues to step S250, where the method ends.

Figure 8:
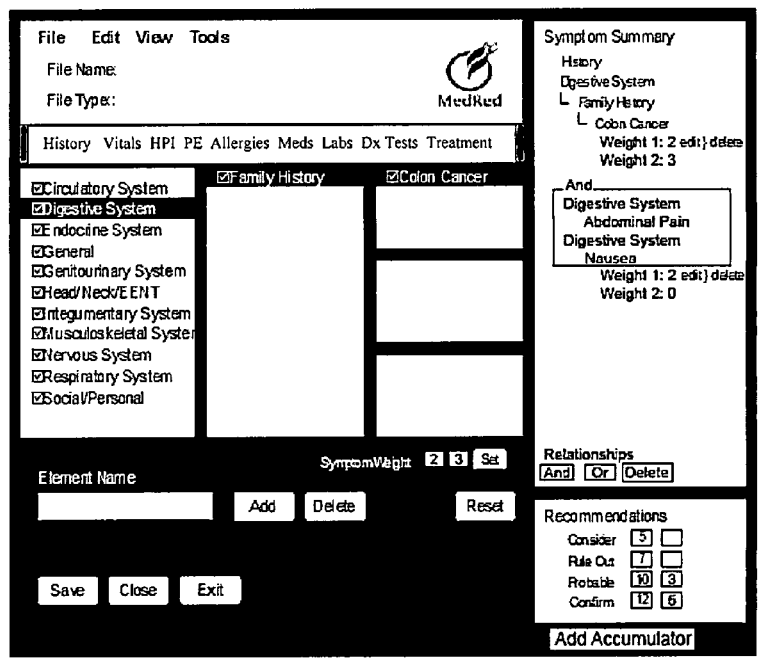
FIG. 8 is an illustration of an exemplary display screen representing primary element tabs.

FIG. 8 is an illustration of an exemplary display screen representing primary element tabs. In FIG. 8, the primary element tabs below the screen header represent the highest level of the hierarchical structure for the protocol files. The tabs may consist of Medical History, Vitals, History of Present Illness (HPI), Physical Exam (PE), Allergies, Medications (Meds), Laboratory (Labs) tests, Diagnosis (Dx) Tests and Treatment. A user may, by clicking on each of these tabs, access a different display screen for entering the protocol information.

Figure 9:
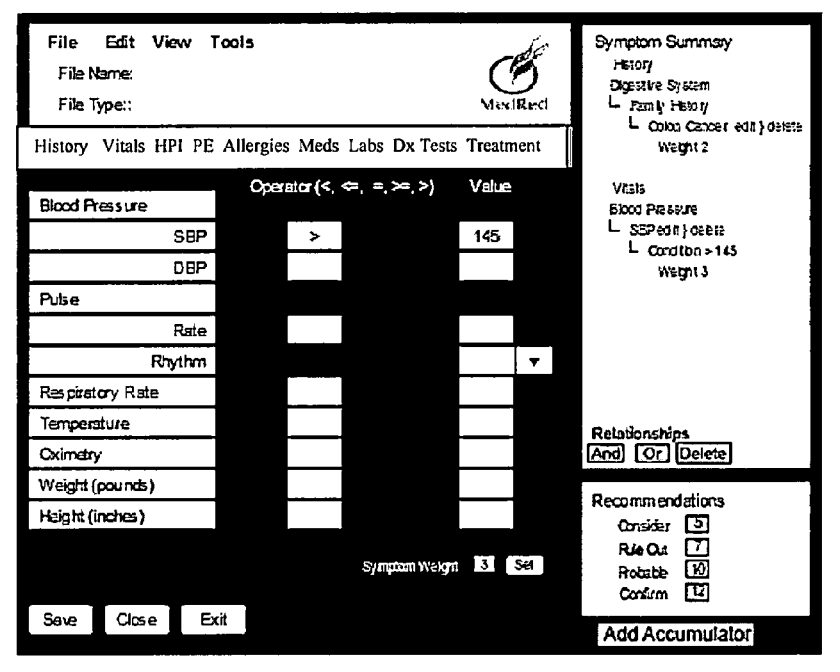

FIG. 9 is an illustration of an exemplary display screen representing an exemplary display screen for vitals. In FIG. 9, the vitals are added to a protocol file by entering a mathematical operator such as "<," "<=," ">=," or ">," and a value for the particular vital. For example, on FIG. 9, the Blood Pressure SBP of a patient is greater than 145.

Figure 10:
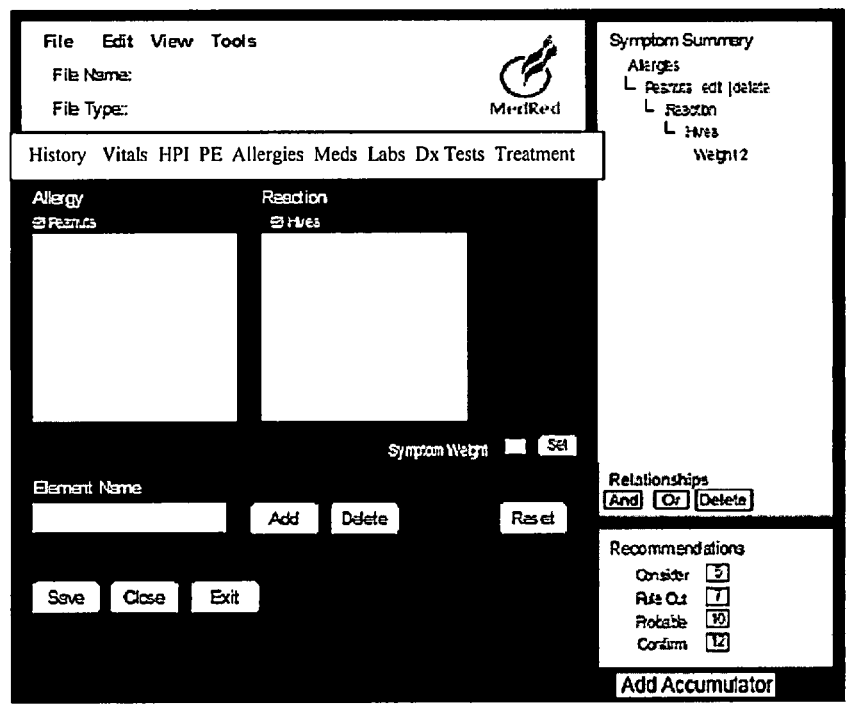
FIG. 10 is an illustration of an exemplary display screen for allergies.

FIG. 10 is an illustration of an exemplary display screen representing an exemplary display screen for allergies. In FIG. 10, to add an allergy to the allergy list, a user may set the focus to the "Allergy" list and enter the allergy in the "Element Name" text box and then click "Add." To delete an allergy from the allergy list, a user may select the allergy from the "Allergy" list and click the "Delete" button.

Figure 11:
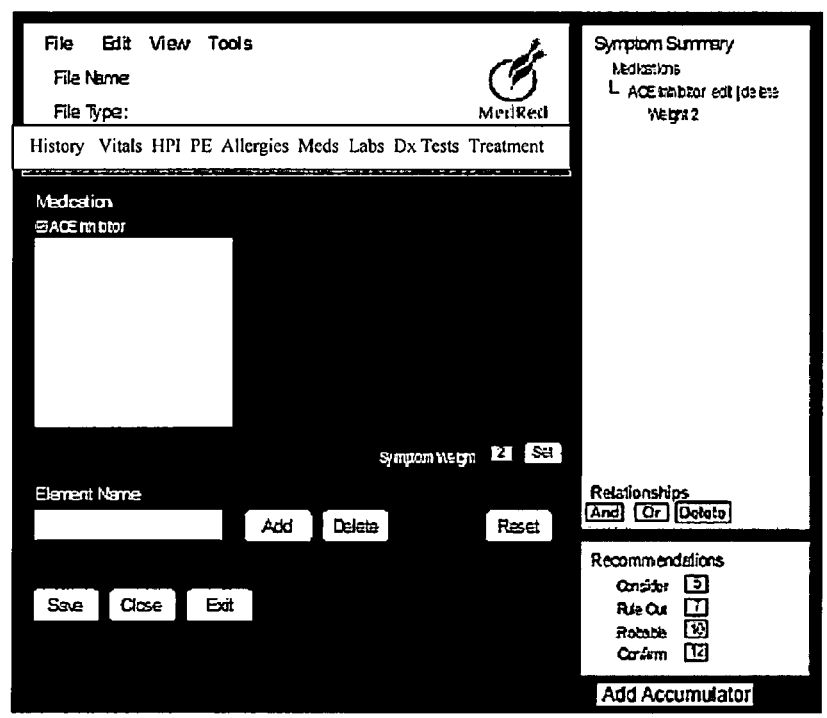
FIG. 11 is an illustration of an exemplary display screen for medications.

FIG. 11 is an illustration of an exemplary display screen for medications. In FIG. 11, to add a medication to the medication list, a user may enter the name of the medication in the "Element Name" text box and click the "Add" button. Similarly, to delete a medication from the list, the user may select the medication in the medication list and click the "Delete" button.

Figure 12:
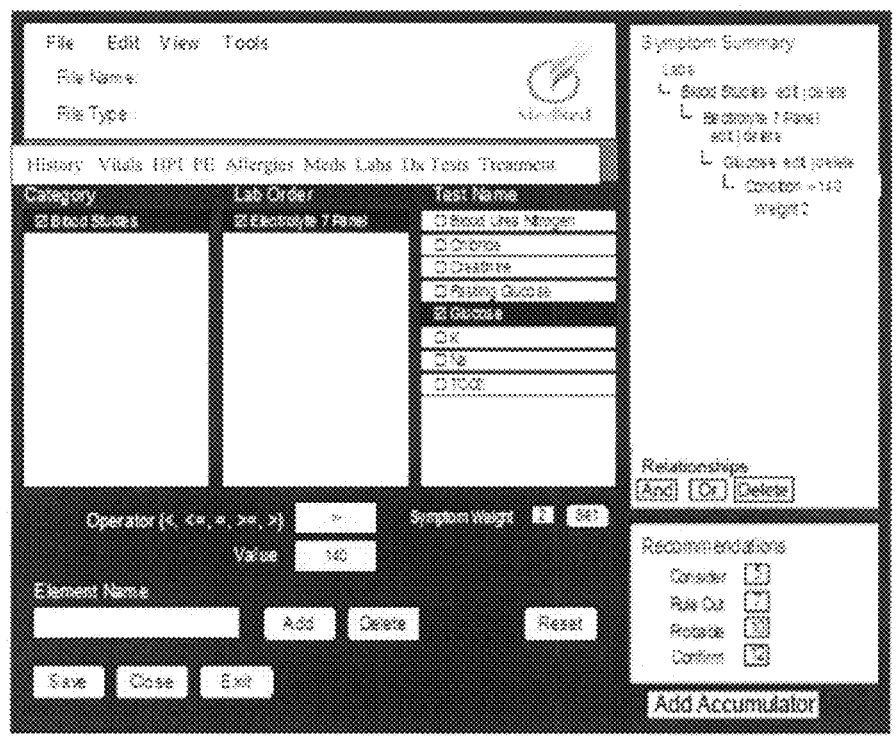
FIG. 12 is an illustration of an exemplary display screen for laboratory tests.

FIG. 12 is an illustration of an exemplary display screen for laboratory tests. In FIG. 12, the procedure for adding and deleting elements is similar to the procedure described above. When selecting elements to add to the protocol file, a user may see the result of the laboratory tests to be positive or negative in the "Value" edit box. The user may also set an operator in the "Operator" box and set a numeric value in the "Value" edit box.

The present invention may be implemented using hardware, software or a combination thereof and may be implemented in one or more computer systems or other processing systems. In one exemplary embodiment, the present invention may be implemented using a Dream Weaver interface and Visual Basic programming. The present invention may also be implemented via three major elements: a Personal Medical Record element, an Authorware element, and a Clinical encounter tool element. These three elements may be functionally coupled in order to achieve a proper diagnosis determination on the basis of a patient's symptoms. According to various exemplary embodiments, a fourth element, a Command and Control Interface, may be added.

The Personal Medical Record element may be the portion where a patient may use the application to manage information pertaining to his/her clinical or medical history. Thus, the patient may create a Personal Medical Record (PMR). This is the application that, for example, contains Quick Look, Vaccination history and other elements described above. Data from this application may be stored in a secured way that is readily accessible to the patient or to a health care operator. The degree to which the application can be accessed by the health care operator may also be set, for example, by the patient.

The Authorware element may be an element that a subject matter expert, without computer programming skills, may use to generate a knowledge base consisting of XML code that may be integrated into a Clinical Encounter Tool in order to provide real time decision support. The user interface for this application may be identical to the user interface for the Clinical Encounter Tool. The subject matter expert may use this tool to, for example, identify the symptoms that are relevant to a particular diagnosis, weigh symptoms relative to a given diagnosis, detail the rationale for particular decisions, and provide detailed treatment recommendations with regard to each individual diagnosis. The output of this application may be an XML knowledge base that may be integrated, in a plug and play fashion, with the Clinical Encounter Tool.

The Clinical Encounter Tool may integrate data from the Personal Medical Record and input from the clinician during the clinical encounter with the decision support knowledge base generated by the subject matter experts using the Authorware. In other words, the Clinical Encounter Tool functionally couples the data from both the Personal Medical Record and the Authorware to achieve the result of providing treatment recommendations, and may be implemented by a health care operator such as, for example, a clinician. The result is real time recommendations regarding diagnosis and treatment as well as readily available explanations regarding the rationale for such recommendations. As discussed above, the user interface for this application may be similar to the user interface for the Authorware application. Additional features may include a plug-and-play integration of knowledge bases, the integration of data from the PMR and the ability of individual Clinical Encounter Tools to synchronize their information with a network-based command and control interface, such as a web-based command and control interface. Additionally, another party such as, for example, a manager, may oversee the operation of the entire system that includes the above-described elements and, for example, obtain situational awareness, direct resources to specific areas or take action based on real-time data. Such a system may also be used in the context, for example, of a network of health care providers.

Additional features may include a plug-and-play integration of knowledge bases, the integration of data from the PMR and the ability of individual clinical encounter tools to synchronize their information with a network-based command and control interface, such as a web-based command and control interface. For example, a Command and Control Interface may allow for the networking and oversight, in real time, of a large number of personnel that may be actively acquiring clinical information and managing patients. In the context of a complex emergency for example, it provides for situational awareness and improved data integration and analysis. Overall features of the system may include secure, two way communication, data integration and point of care decision support.

Figure 13:
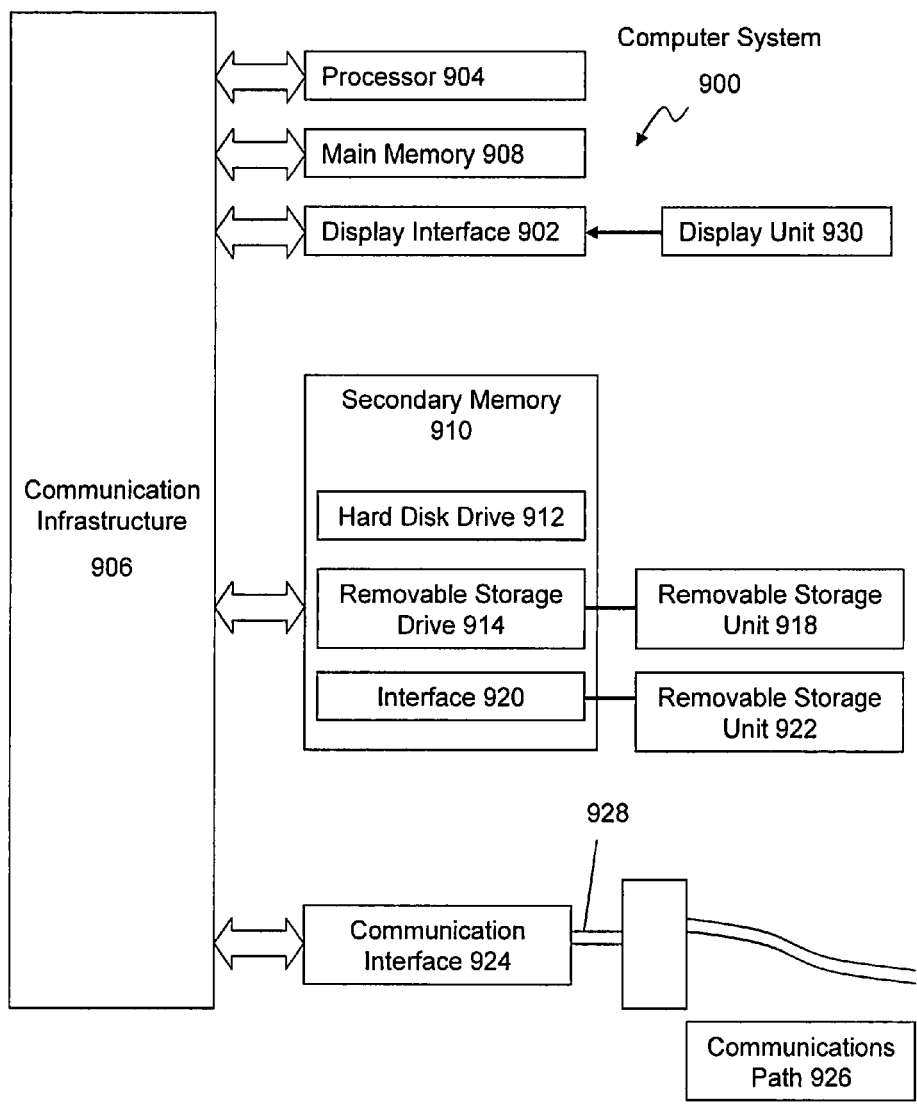
FIG. 13 illustrates an exemplary system diagram of various hardware components and other features, in accordance with an embodiment of the present invention.

In one exemplary embodiment, the invention is directed toward one or more computer systems capable of carrying out the functionality described herein. An example of such a computer system 900 is shown in FIG. 13.

Computer system 900 includes one or more processors, such as processor 904. The processor 904 is connected to a communication infrastructure 906 (e.g., a communications bus, cross-over bar, or network). Various software embodiments are described in terms of this exemplary computer system. After reading this description, it may become apparent to a person skilled in the relevant art(s) how to implement the invention using other computer systems and/or architectures.

Computer system 900 can include a display interface 902 that forwards graphics, text, and other data from the communication infrastructure 906 (or from a frame buffer not shown) for display on the display unit 930. Computer system 900 also includes a main memory 908, preferably random access memory ("RAM"), and may also include a secondary memory 910. The secondary memory 910 includes, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a well-known manner. Removable storage unit 918, represents a floppy disk, magnetic tape, optical disk, etc., which is read by and written to removable storage drive 914. As may be appreciated, the removable storage unit 918 includes a computer usable storage medium having stored therein computer software and/or data.

In alternative embodiments, secondary memory 910 includes other similar devices for allowing computer programs or other instructions to be loaded into computer system 900. Such devices include, for example, a removable storage unit 922 and an interface 920. Examples of such may include a program cartridge and cartridge interface (such as that found in video game devices), a removable memory chip (such as an erasable programmable read only memory ("EPROM"), or programmable read only memory ("PROM")) and associated socket, and other removable storage units 922 and interfaces 920, which allow software and data to be transferred from the removable storage unit 922 to computer system 900.

Computer system 900 also includes, for example, a communications interface 924. Communications interface 924 allows software and data to be transferred between computer system 900 and external devices. Examples of communications interface 924 may include a modem, a network interface (such as an Ethernet card), a communications port, a Personal Computer Memory Card International Association ("PCMCIA") slot and card, etc. Software and data transferred via communications interface 924 are in the form of signals 928, which may be electronic, electromagnetic, optical or other signals capable of being received by communications interface 924. These signals 928 are provided to communications interface 924 via a communications path (e.g., channel) 926. This path 926 carries signals 928 and may be implemented using wire or cable, fiber optics, a telephone line, a cellular link, a radio frequency ("RF") link and/or other communications channels. In this document, the terms "computer program medium" and "computer usable medium" are used to refer generally to media such as a removable storage drive 914, a hard disk installed in hard disk drive 912, and signals 928. These computer program products provide software to the computer system 900. The invention is directed to such computer program products.

Computer programs (also referred to as computer control logic) are stored in main memory 908 and/or secondary memory 910. Computer programs may also be received via communications interface 924. Such computer programs, when executed, enable the computer system 900 to perform the features of the present invention, as discussed herein. In particular, the computer programs, when executed, enable the processor 904 to perform the features of the present invention. Accordingly, such computer programs represent controllers of the computer system 900.

In an embodiment where the invention is implemented using software, the software may be stored in a computer program product and loaded into computer system 900 using removable storage drive 914, hard drive 912, or communications interface 924. The control logic (software), when executed by the processor 904, causes the processor 904 to perform the functions of the invention as described herein. In another embodiment, the invention is implemented primarily in hardware using, for example, hardware components, such as application specific integrated circuits ("ASICs"). Implementation of the hardware state machine so as to perform the functions described herein may be apparent to persons skilled in the relevant art(s).

In yet another embodiment, the invention is implemented using a combination of both hardware and software.

Figure 14:
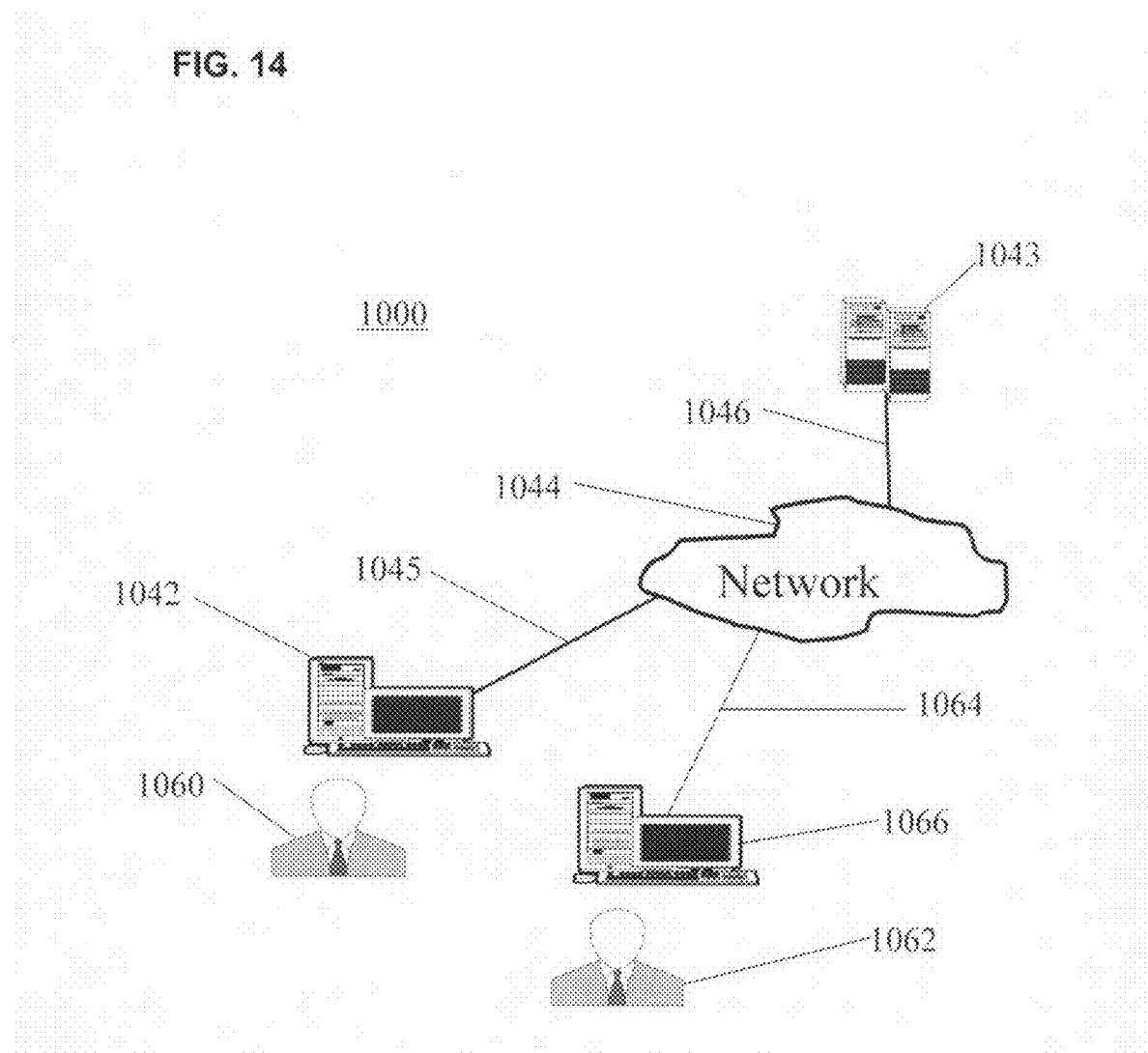
FIG. 14 illustrates an exemplary system diagram of various hardware components and other features in accordance with an embodiment of the present invention of the present invention.

FIG. 14 shows a system 1000 usable in accordance with an embodiment of the present invention. The system 1000 includes an accessor 1060 (also referred to interchangeably herein as a "user") at a terminal 1042. In one exemplary embodiment, data for use in accordance with the present invention is, for example, input and/or accessed by the accessor 1060 via the terminal 1042, such as a personal computer (PC), minicomputer, mainframe computer, microcomputer, telephonic device, or wireless device, such as a personal digital assistant ("PDA") or a hand-held wireless device, coupled to a server 1043, such as a PC, minicomputer, mainframe computer, microcomputer, or other device having a processor and a repository for data and/or connection to a processor and/or repository for data, via, for example, a network 1044, such as the Internet or an intranet, and couplings 1045, 1064. The couplings 1045, 1064 include, for example, wired, wireless, or fiber-optic links. In another embodiment, the method and system of the present invention operate in a stand-alone environment, such as on a single terminal.

Furthermore, while this invention has been described in conjunction with the exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

What is claimed is:

1. A computer-implemented method for creating a data repository for diagnosis and/or treatment determination, the data repository containing a baseline representation of at least one diagnosis, condition and/or treatment, the baseline representation including a combination of signs and symptoms that are weighted and assigned thresholds, the computer including a processor and a data repository, the method comprising:

receiving via the processor the at least one diagnosis, condition and/or treatment;

receiving the combination of signs and symptoms that is associated with the at least one diagnosis, condition and/or treatment;

attaching a weight to each of the signs and symptoms based on the significance of each of the signs and symptoms to each diagnosis, condition and/or treatment;

assigning a threshold to each of the weighted signs and symptoms relative to each diagnosis, condition and/or treatment; and rendering the baseline representation accessible by charting the weighted medical signs and symptoms of a patient that are greater than the assigned thresholds;

wherein a depiction of the baseline representation is used for comparison of the combination of weighted signs and symptoms with a combination of the medical signs and symptoms of the patient.

2. The method of claim 1, wherein the received at least one diagnosis, condition and/or treatment are updated in a memory on the basis of current medical knowledge.

3. The method of claim 1, wherein the baseline representation is rendered accessible via a user-generated query.

4. A computer-implemented method for determining a diagnosis and/or treatment using a data repository, the data repository containing a baseline representation of at least one diagnosis, condition and/or treatment, the baseline representation having a combination of baseline signs and symptoms, each being weighted and assigned baseline thresholds based on a significance to an associated diagnosis, condition and/or treatment, the computer comprising a processor and a data repository, the method comprising:

receiving via the processor a plurality of symptoms and signs for a patient;

attaching a weight to each of the symptoms and signs for the patient based on the significance of each of the symptoms and signs for the patient to each diagnosis, condition and/or treatment;

assigning a threshold to each of the weighted signs and symptoms for the patient relative to each diagnosis, condition and/or treatment;

comparing a combination of the received symptoms and signs for the patient that are greater than the assigned thresholds to the combination of weighted baseline signs, symptoms and/or indications of the baseline representation that are reater than the baseline thresholds; and generating one or more patient diagnosis, condition and/or treatment recommendation based on the comparison.

5. The method of claim 4, wherein the baseline signs and symptoms have been previously stored in the data repository.

6. A system for diagnosis and/or treatment determination including a data repository, the data repository containing a baseline representation of at least one diagnosis, condition and/or treatment, the baseline representation having a combination of baseline signs and symptoms, each being weighted and assigned baseline thresholds based on a significance to an associated diagnosis, condition and/or treatment, the system comprising:

a processor;

a user interface configured to function via the processor; and another repository accessible by the processor; wherein the system is configured to:

receive via the processor a plurality of symptoms and signs for a patient;

attach a weight to each of the symptoms and signs for the patient based on the significance of each of the symptoms and signs for the patient to each diagnosis, condition and/or treatment;

assign a threshold to each of the weighted signs and symptoms for the patient relative to each diagnosis, condition and/or treatment;

compare a combination of the received symptoms and signs for the patient that are greater than the assigned thresholds to the combination of weighted baseline signs, symptoms and/or indications of the baseline representation that are greater than the baseline thresholds; and generate one or more patient diagnosis, condition and/or treatment recommendation based on the comparison.

7. The system of claim 6, wherein the user interface is configured to display a screen, wherein the screen comprises at least one of a summary section, a patient profile section, a contacts and insurance section, a medication, a medical conditions section, a laboratory data section, a radiology section, a mammography section, a doctor visits section, a procedures section, a prevention/screening section, an immunization section, a private information section, a document inbox section, and an account management section.

8. The system of claim 7, wherein at least one of the sections are accessible by the user.

9. The system of claim 7, wherein data displayed in the sections is updated with new information.

10. The system of claim 6, wherein a unique identifier is assigned to each patient.

11. The system of claim 10, wherein the received patient symptoms and signs and the generated diagnosis and/or treatment recommendation are accessible for each patient by using the unique identifier.

12. The system of claim 6, wherein the one or more diagnosis and/or treatment recommendation is provided by labeling the diagnosis and/or treatment recommendation at least one of consider, rule out, probable and confirm.

13. The system of claim 6, wherein the processor is housed on a terminal selected from a group consisting of a personal computer, a minicomputer, a main frame computer, a microcomputer, a hand held device, and a telephonic device.

14. The system of claim 6, wherein the processor is housed on a server selected from a group consisting of a personal computer, a minicomputer, a microcomputer, and a main frame computer.

15. The system of claim 14, wherein the server is coupled to a network via a coupling selected from a group consisting of a wired connection, a wireless connection, and a fiberoptic connection.

16. The system of claim 6, wherein the other repository is housed on a server coupled to a network.

17. The system of claim 6, further comprising a hand-held interface device that allows the user to access the other repository.

18. A computer program product including a computer usable medium having control logic stored therein for causing a computer to determine diagnosis and/or treatment via a data repository, the data repository containing a baseline representation of at least one diagnosis, condition and/or treatment, the baseline representation having a combination of baseline signs and symptoms each being weighted and assigned baseline thresholds based on a significance to an associated diagnosis, condition and/or treatment, the control logic comprising:

means for receiving via the processor a plurality of symptoms and signs for a patient;

means for attaching a weight to each of the symptoms and signs for the patient based on the significance of each of the symptoms and signs for the patient to each diagnosis, condition and/or treatment;

means for assigning a threshold to each of the weighted signs and symptoms for the patient relative to each diagnosis, condition and/or treatment;

means for comparing a combination of the received symptoms and signs for the patient that are greater than the assigned thresholds to the combination of weighted baseline signs, symptoms and/or indications of the baseline representation that are greater than the baseline thresholds; and means for generating one or more patient diagnosis, condition and/or treatment recommendation based on the comparison.

19. A system for determining a diagnosis and/or treatment via a data repository, the data repository containing a baseline representation of at least one diagnosis, condition and/or treatment, the baseline representation and having a combination of baseline signs and symptoms, each being weighted based on a significance to an associated diagnosis, condition and/or treatment, the system comprising:

means for receiving via the processor a plurality of symptoms and signs for a patient;

means for attaching a weight to each of the symptoms and signs for the patient based on the significance of each of the symptoms and signs for the patient to each diagnosis, condition and/or treatment;

means for assigning a threshold to each of the weighted signs and symptoms for the patient relative to each diagnosis, condition and/or treatment;

means for comparing a combination of the received symptoms and signs for the patient that are greater than the assigned thresholds to the combination of weighted baseline signs, symptoms and/or indications of the baseline representation that are greater than the baseline thresholds; and means for generating one or more patient diagnosis, condition and/or treatment recommendation based on the comparison.

20. The method of claim 1, wherein the data repository is customized to specific practice areas or environments.

21. The method of claim 1, wherein rendering the baseline representation accessible comprises rendering the baseline representation accessible via at least one of a graphical user interface and a network.

22. A system for creating a data repository for diagnosis and/or treatment determination, the data repository containing a baseline representation of at least one diagnosis, condition and/or treatment, the baseline representation including a combination of signs and symptoms that are weighted and assigned thresholds, the system comprising:

a processor;

a user interface configured to function via the processor; and another repository accessible by the processor;

wherein the system is configured to:

receive via the processor the at least one diagnosis, condition and/or treatment;

receive the combination of signs and symptoms that is associated with the at least one diagnosis, condition and/or treatment;

attach a weight to each of the signs and symptoms based on the significance of each of the signs and symptoms to each diagnosis, condition and/or treatment;

assign a threshold to each of the weighted signs and symptoms relative to each diagnosis, condition and/or treatment; and render the baseline representation accessible by charting the weighted medical signs and symptoms of a patient that are greater than the assigned thresholds;

wherein a depiction of the baseline representation is used for comparison of the combination of weighted signs and symptoms with a combination of the medical signs and symptoms of the patient.

23. The system of claim 22, wherein the received at least one diagnosis, condition and/or treatment are updated in a memory on the basis of medical knowledge.

24. The system of claim 22, wherein the baseline representation is rendered accessible via a user-generated query.

25. The method of claim 4, wherein the diagnosis and/or treatment are customized to specific practice areas or environments.

26. The method of claim 4, wherein the one or more patient diagnosis and/or treatment recommendation are provided via at least one of a graphical user interface and a network.

27. The method of claim 1, wherein the baseline representation comprises aggregate symptom complexes.

28. The method of claim 4, wherein the baseline representation comprises aggregate symptom complexes.

29. The system of claim 6, wherein the baseline representation comprises aggregate symptom complexes.

30. The computer program product of claim 18, wherein the baseline representation comprises aggregate symptom complexes.

31. The system of claim 19, wherein the baseline representation comprises aggregate symptom complexes.

32. The system of claim 22, wherein the baseline representation comprises aggregate symptom complexes.

33. The method of claim 4, wherein the computer is separately located at a patient site.

34. The system of claim 6, wherein the system is separately located at a patient site.

35. The method of claim 4, wherein:

the plurality of symptoms and signs for the patient is received via a questionnaire, and the method further comprises the patient responding to the questionnaire by choosing between more than two possible answers.

36. The system of claim 6, wherein:

the plurality of symptoms and signs for the patient is received via a questionnaire, and the system is further configured to have the patient respond to the questionnaire by choosing between more than two possible answers.

37. The method of claim 1, wherein the attached threshold is determined independently of the patient.

38. The method of claim 4, wherein the attached threshold is determined independently of the patient.

* * * * *